(12) United States Patent
Scommegna et al.

(10) Patent No.: US 10,342,639 B2
(45) Date of Patent: *Jul. 9, 2019

(54) EXPANSION SCREW FOR ORTHODONTIC APPLIANCES

(71) Applicant: LEONE S.P.A., Sesto Fiorentino (FI) (IT)

(72) Inventors: Gabriele Scommegna, Tavarnuzze Impruneta (IT); Maurizo Dolfi, Florence (IT)

(73) Assignee: LEONE S.P.A., Sesto Fiorentino (FI) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 15/547,230

(22) PCT Filed: Dec. 15, 2015

(86) PCT No.: PCT/IT2015/000308
§ 371 (c)(1),
(2) Date: Jul. 28, 2017

(87) PCT Pub. No.: WO2016/120896
PCT Pub. Date: Aug. 4, 2016

(65) Prior Publication Data
US 2018/0008376 A1    Jan. 11, 2018

(30) Foreign Application Priority Data

Jan. 31, 2015   (IT) .................. FI2015A0019

(51) Int. Cl.
*A61C 7/10*    (2006.01)

(52) U.S. Cl.
CPC ..................... *A61C 7/10* (2013.01)

(58) Field of Classification Search
CPC ...................................... A61C 7/10
See application file for complete search history.

(56) References Cited

U.S. PATENT DOCUMENTS 3,284,902 A  *  11/1966  Dillberg .............. A61C 7/10
                                                    433/7
3,921,294 A  *  11/1975  Wallshein ............ A61C 7/10
                                                    433/7

(Continued)

FOREIGN PATENT DOCUMENTS

DE       32 41 105 A1    5/1984
DE       200 10 279 U1   8/2000

(Continued)

*Primary Examiner* — Heidi M Eide
(74) *Attorney, Agent, or Firm* — McGlew and Tuttle, P.C.

(57) ABSTRACT

Expansion screw for orthodontic appliances, including at least one stem (1) with at least a threaded portion (10) extending along the longitudinal extension of the stem (1), at least one receiving body (3) for receiving the threaded portion (10) provided with a receiving hole complementarily shaped with respect to the threaded portion (10) so as to allow its screwing, guide structure (2) for guiding the at least one receiving body (3), driving mechanism (11, 12) for driving the stem (1), and including a positioning tab (6) composed of multiple parts (60, 61) associated with each other to support the expansion screw (100) when the orthodontic appliance is made, the tab (6) being provided with at least an appendix (62) that can be stably inserted into a cavity (12) exhibited by the expansion screw (100).

17 Claims, 7 Drawing Sheets

(56) References Cited

U.S. PATENT DOCUMENTS

| | | | |
|---|---|---|---|
| 4,482,318 A | | 11/1984 | Förster |
| 5,323,189 A | * | 6/1994 | Contreras ............... G02C 5/146 |
| | | | 351/118 |
| 5,472,344 A | | 12/1995 | Binder et al. |
| 5,975,894 A | * | 11/1999 | Pozzi ....................... A61C 7/10 |
| | | | 433/7 |
| 2007/0218416 A1 | * | 9/2007 | Keles ....................... A61C 7/10 |
| | | | 433/7 |

FOREIGN PATENT DOCUMENTS

| | | |
|---|---|---|
| EP | 0 868 888 A1 | 10/1998 |
| GB | 641139 A | 8/1950 |
| IT | 1163244 B | 4/1987 |
| IT | 0001278739 B1 | 11/1997 |

\* cited by examiner

EXPANSION SCREW FOR ORTHODONTIC APPLIANCES

The present invention relates to an expansion screw for orthodontic appliances, in particular for manufacturing orthodontic appliances comprising plates made of synthetic resin materials. The invention further concerns a tool for handling and positioning the orthodontic screw during the forming step of the plate that receives it.

A bidirectional expansion screw for orthodontics generally comprises a central stem with counter-rotating threads on the sides with a central "maneuvering" portion of greater diameter, to allow its rotation by means of a tool plug insertable into the recesses or holes provided on its surface. The stem of the screw is associated with two guides constituted by cylindrical parallel rods interconnected by metal blocks which have longitudinal holes in which the same rods are made to pass, so as to form a guide assembly for handling the blocks with the corresponding separate portions of the orthodontic plate. In each of the blocks connecting the guide rods is provided a threaded hole intended to receive a corresponding side of the central stem. Expansion screws of this type are disclosed in IT1163244, U.S. Pat. No. 5,472,344, GB641139, as well as in EP868888 and De20010279.

One aim of the present invention is to provide a new type of expansion screw having a structure offering a higher functionality, both during the realization of the orthodontic plat and in configuration of use.

This result is achieved by providing an expansion screw for orthodontic appliances having the features listed in claim 1. Other features of the present invention are the subject of the dependent claims.

The present invention offers the following advantages: the manufacturing process is improved; the interaction between the stem and the receiving bodies in which it is screwed is also improved; the expansion screw exhibits a higher resistance to mechanical stresses; the manufacturing and the use of the orthodontic appliance are simplified.

These and other advantages and features of this invention will be best understood by anyone skilled in the art from the following description and with the help of the attached drawings given as a practical exemplification of the invention, but not to be considered in a limitative sense, wherein.

With reference to the attached drawings, an expansion screw (100) for orthodontic resin appliances comprising resin plates according to the present invention comprises at least one stem (1) with at least a threaded stem portion (10) extending along the stem (1). The screw (100) further comprises at least one receiving body (3) for the threaded stem portion (10) of the stem (1), provided with a complementarily threaded hole for receiving said portion (10) so as to allow the screwing thereof, guide means (2) for guiding said at least one receiving body (3) and driving means (11, 12) for making the stem (1) to rotate about its own axis.

Figure 1:
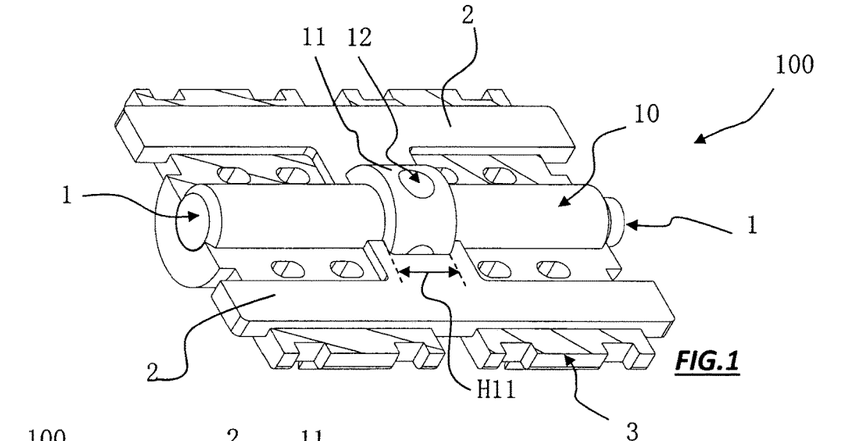
FIG. 1 is a perspective view with sectioned parts of a possible embodiment of an orthodontic screw in accordance with the present invention.
Figure 2:
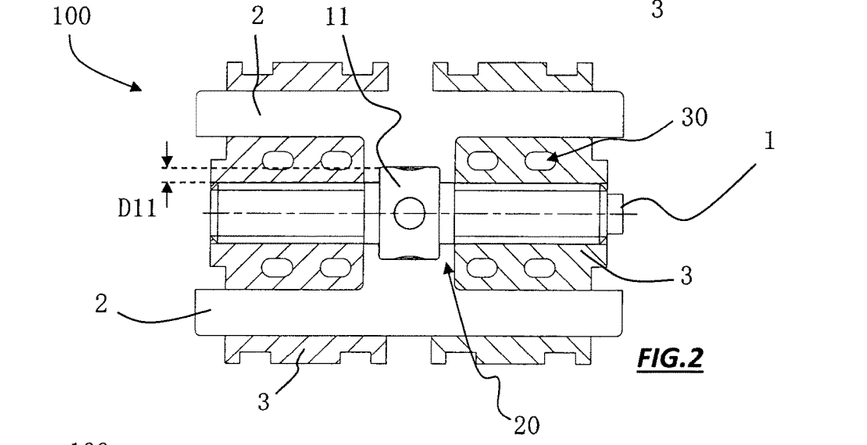
FIGS. 2 and 3 are plan views with sectioned parts of the example shown in FIG. 1, represented in two different positions, respectively, the minimum and maximum expansion position.
Figure 3:
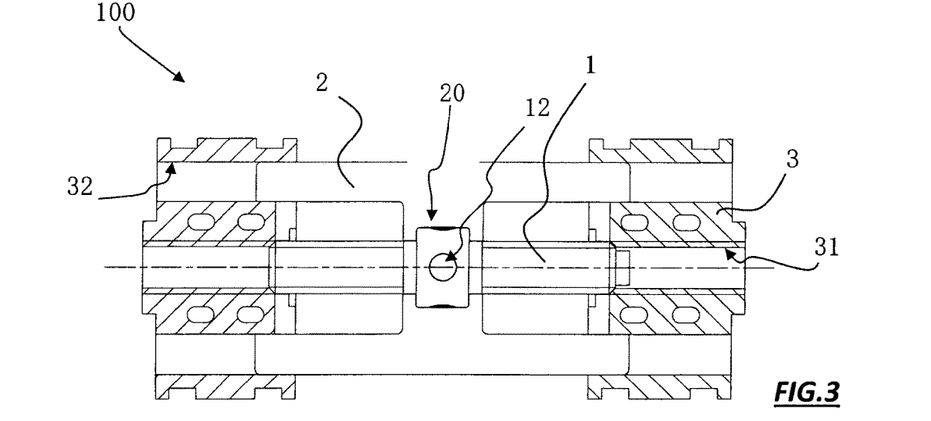
Figure 4:
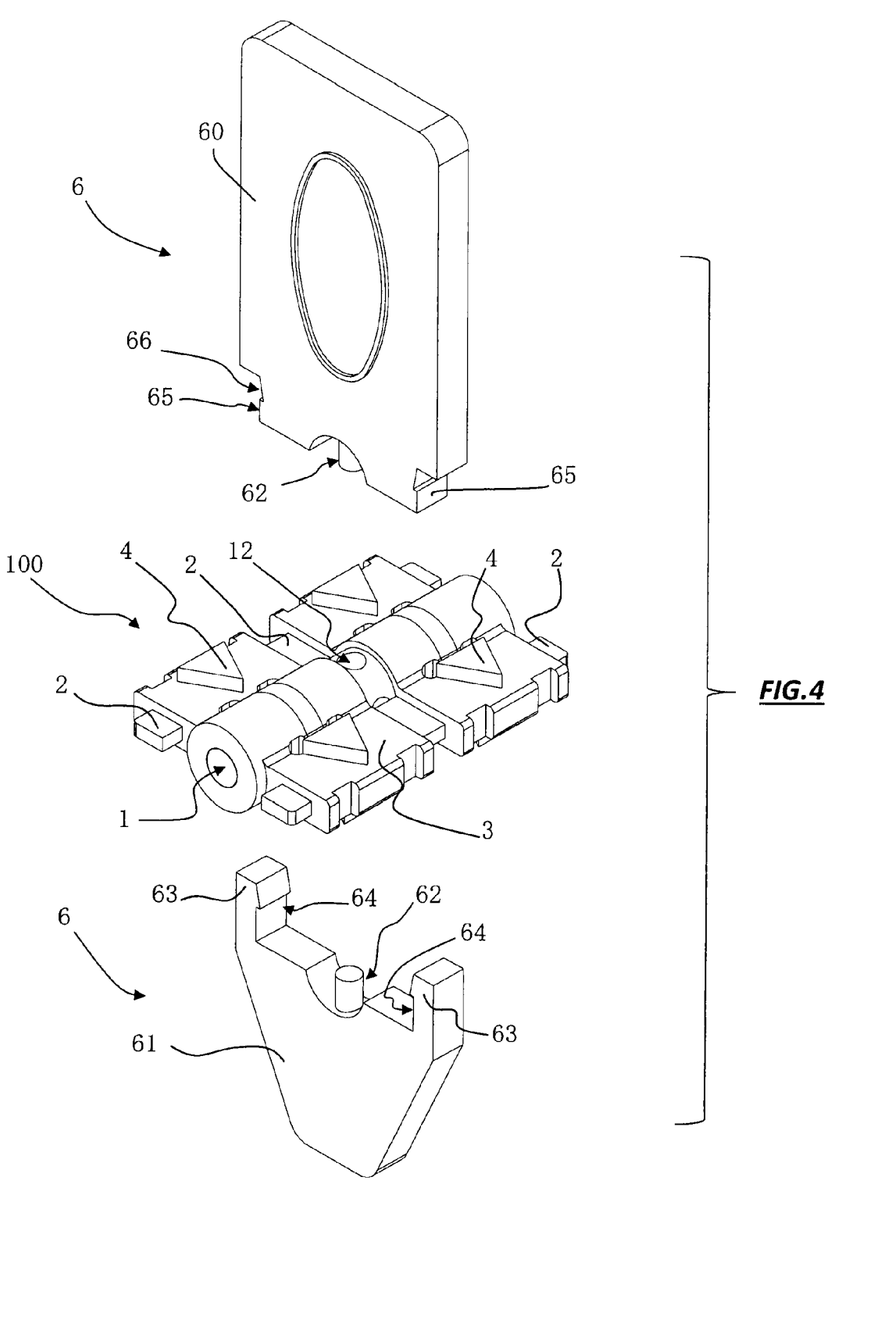
FIG. 4 is an exploded perspective view of the example shown in the previous drawings, with a tool for its handling that can be used, in particular, during the positioning of the screw for the association to the resin plates which form the orthodontic appliance.
Figures 5, 7:
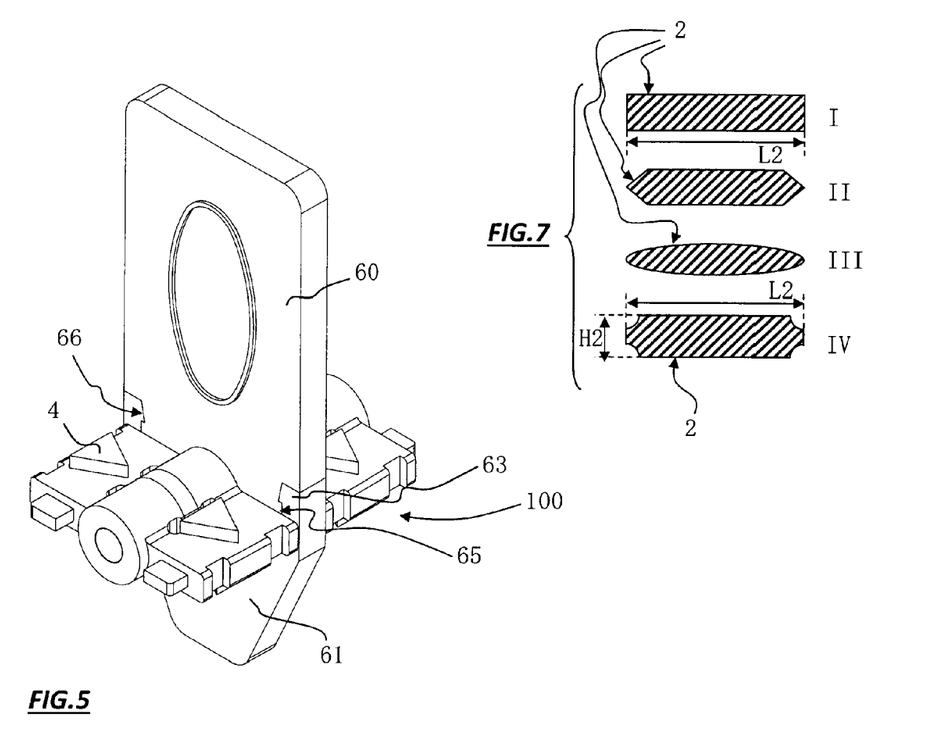
FIG. 5 shows the example of FIG. 4 in the assembled configuration.
FIG. 7 shows cross-sectional views of possible embodiments of the guide elements of an orthodontic screw according to the invention.
Figure 6:
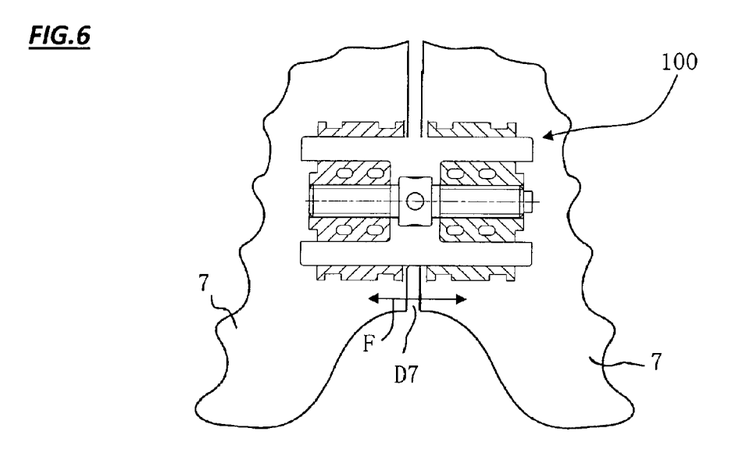
FIG. 6 is a schematic plan view representing an orthodontic plate provided with an orthodontic screw made according to the present invention, the orthodontic screw being represented in a plan view with sectioned parts.

With reference to FIGS. 1-7, the screw can be of the bidirectional type, i.e. of the type comprising two differently threaded opposite stem portions (10) (for example anti-clockwise threading to the left and clockwise threading to the right) to determine, in a known way, the contemporary spacing of the two receiving bodies (3) with respect to the central driving portion (11) of the screw to cause the corresponding distancing of the portions (7) of an orthodontic resin base plate; in FIG. 6 the arrow (F) shows the possible movements of the plate portions (7) and (D7) denotes the space between the same portions of the orthodontic plate.

The orthodontic appliance shown in FIG. 6 is formed by the screw (100) and the plate including said portions (7). The base plate has side edges intended to contact the lingual side of the teeth. The screw (100) is incorporated into the resin of the base plate according to methods known to those skilled in the art.

Figure 13:
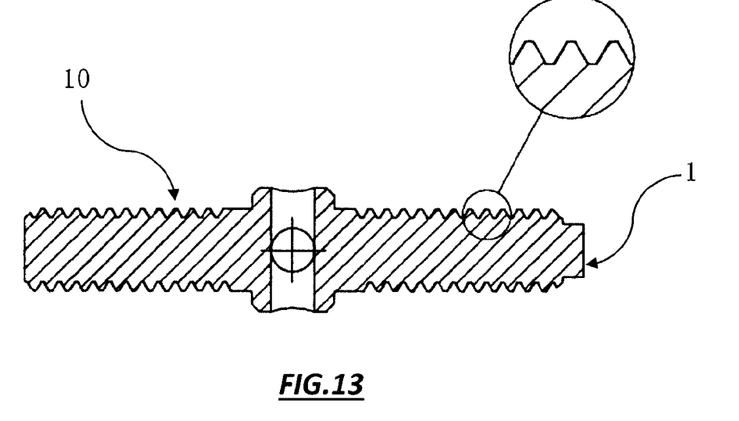
FIG. 13 represents a possible embodiment of the screw (1)

The threads of the threaded stem portions (10) of the screw can have a trapezoidal profile, as shown by way of example in FIG. 13, thus offering a greater resistant cross section, or they can have any other suitable profile, being entirely eliminated the construction constraints related to the need of threading the receiving body. In fact, the threads (10) are copied perfectly inside the receiving body (3) when the latter is formed, as further described in the following.

The central driving portion (11) is substantially cylindrical; in particular, the central portion (11) extends along the stem (1) for a first value (H11) and projects radially from the central driving portion of the stem (1) for a second value (D11). The holes (12) provided by the portion (11) are used to obtain the rotation of the stem (1) for the operation of the orthodontic screw (100) by means of a tool that can be inserted into said holes.

According to the present invention, the hole (31) of the receiving body (3) has a longitudinal extension substantially corresponding to that of the threaded portion (10) of the stem (1). In practice, the body (3) is made of a technopolymer that, in phase of realization of the screw (100), is associated to the other parts of the orthodontic screw (100). When the orthodontic screw (100) is manufactured, the stem (1) and the guide means (2) are embedded in the technopolymer that constitutes the receiving body (3). In this way, the threaded portions of the stem (1) are completely covered by the technopolymer of the receiving body, thus offering a double advantage: the threads (30) of the body (3) are exactly complementary to the threads (10) of the stem (1) and the threads (10) do not remain uncovered and, therefore, are not affected by the subsequent incorporation into the resin of the base plate during the formation of the orthodontic appliance. In fact, the next phase of the process provides for the embedding of the orthodontic screw (100) in the resin of the base plate; in this way, the friction (due to the engagement between stem 1 and body 3) will be independent from the characteristics of the resin chosen for making the base plate and will not depend on the process chosen for manufacturing the latter. Suitable technopolymers can be, for example, polyoxymethylene (POM), polyamide (PA), polysulfone (PPSU) or talc filled polypropylene.

In addition, the guide means (2) advantageously comprise a substantially flat body with a cross-section having a first dimension (H2) substantially smaller than a second dimension (L2). FIG. 7 shows some possible embodiments of the guides (2). The flat shape of the guides (2) allows for improved force transmission; in practice, since these guides are substantially flat, the transmission of forces to the teeth of the patient is more gradual due to the higher flexibility thus acquired by the device that ensures a corresponding progressive release of forces. By suitably sizing the guides (2) it is possible to adjust the flexibility of the orthodontic device, i.e. the gradual release of the forces. This leads to advantages in the step of positioning the appliance in the oral cavity after a possible interruption of the therapy.

Figure 11:
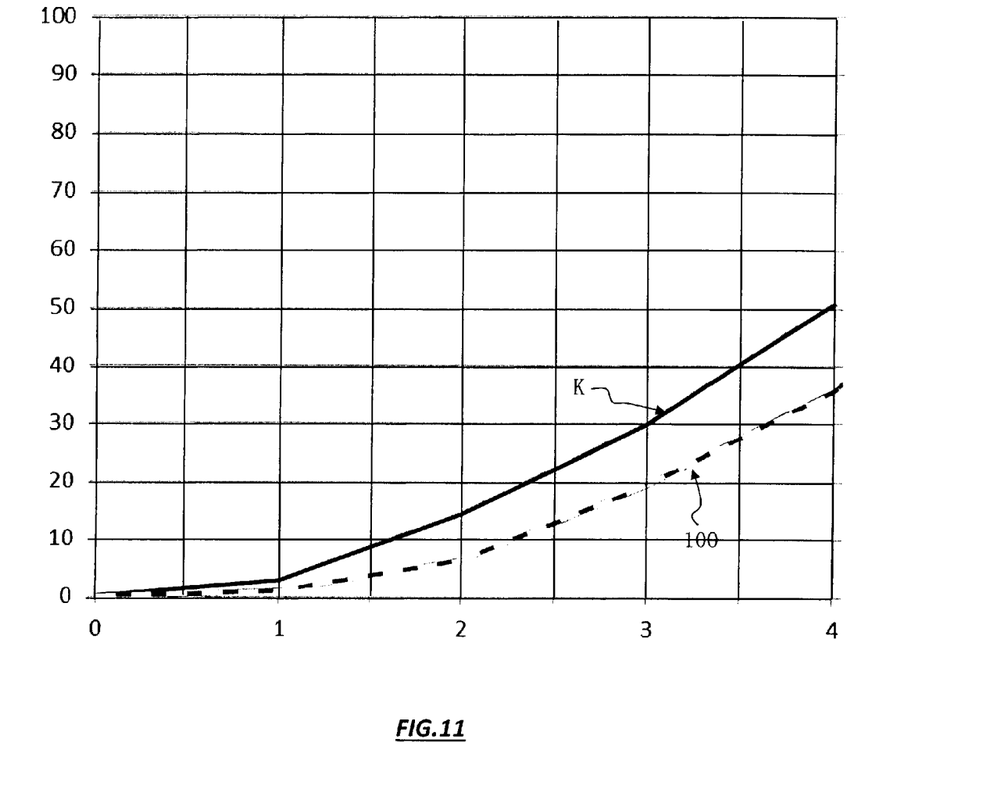
FIG. 11 is a graph that illustrates the difference between the compression response provided by means of an orthodontic screw made according to the present invention and by means of a conventional orthodontic screw.

FIG. 11 is a graph showing the results of tests concerning the stiffness response to compression of a screw with a plastic body manufactured in accordance with the present invention in comparison with a standard steel screw manufactured by Leone Spa, model No. A0805, identified with (K) in the graph.

Figure 12:
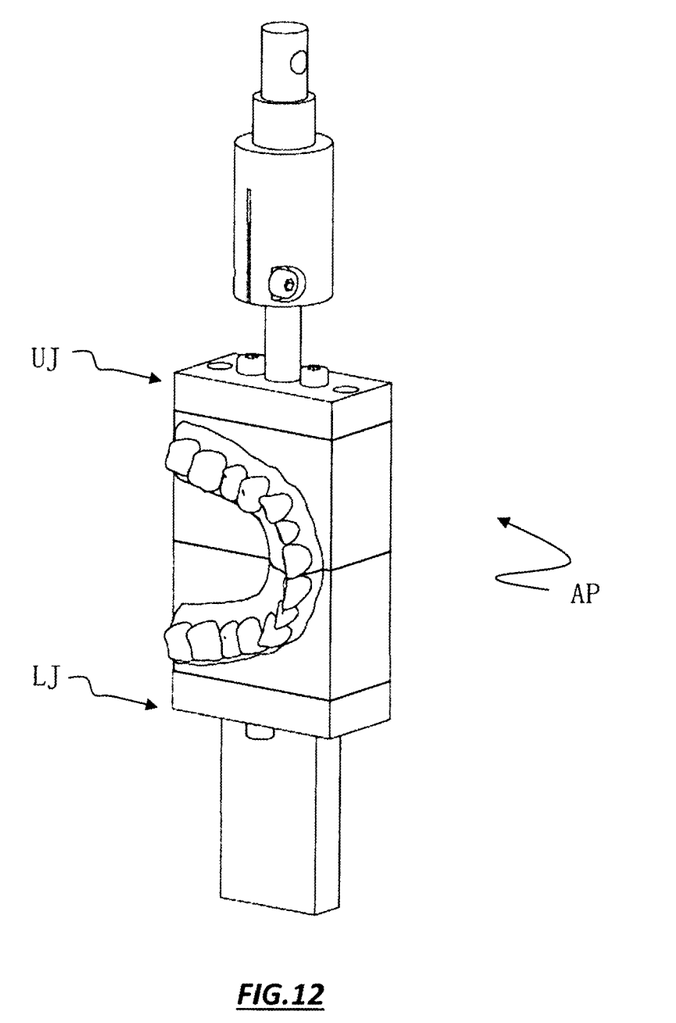
FIG. 12 schematically represents an apparatus designed to obtain the graph of FIG. 11.

The tests performed by the applicant allowed an instrumental check of the magnitude and the releasing conditions of a force by the expansion screw (100) described above compared to a standard screw (K). In particular it has been verified that the greater flexibility of the screw (100) with plastic bodies and rectangular cross section guides (AISI 301/3021, thickness 0.6 mm, screw thread M2) instead of circular cross section allows insertion in a same orthodontic model with a greater number of initial activations as compared to the conventional more rigid expansion screw entirely made of steel and circular cross section guides (that in the tests were of a diameter of 1.5 mm, screw thread M22). For executing the test, removable plates were made adapted to fit to the same orthodontic model; the plates were identical to each other, except, for the expansion screw positioned inside them. Each of the resin plates was divided into two halves in turn locked to two opposite supports, one clamped by a lower clamp (LJ) and the other clamped by an upper clamp (UJ) of a testing apparatus (AP) made by the same applicant. The forces were sensed by load cells.

The graph in FIG. 11 shows the stiffness curves of the two devices subjected to the test, starting from a closed screw configuration. From the curves it can be seen that the orthodontic screw (100) in accordance with the invention is characterized by a lower stiffness than a conventional expander (K). In other words, for an equal number of activations, the expander of the present invention performs a lower compression force and it is possible to fit it in the model with a higher number of activations, i.e. a higher number of turns of the screw, compared to the conventional screw-operated expander. Referring to the detected values, it is noted that with two activations, corresponding to an expansion of 0.4 mm, the screw of the conventional type (K) determines a load comprised between 10 and 20 N, i.e. about 15 N, while the screw according to the invention (100) determines a load comprised between 0 and 10 N, i.e. about 7 N; with four activations, corresponding to an expansion of 0.8 mm, the screw of the conventional type (K) determines a load higher than 50 N, i.e. about 51 N, while the screw according to the invention (100) determines a load comprised between 30 and 40 N, i.e. about 36 N.

Furthermore, since the body (3) is made of a technopolymer, instead of a metal material, it can be colored and more visible.

The guide means (2) are constituted by a body which extends towards said driving portion (11) copying its profile. In particular, since said driving portion (11) is cylindrical, said guide means (2) are provided with an appendix (20), which interacts with the driving portion (11), provided with a cavity with rectangular profile extending along the longitudinal direction of the stem (1) and radially to such direction. The longitudinal and the radial length of said cavity correspond respectively to said first (H11) and said second value (D11).

With reference to the drawings (in particular FIGS. 1-7), the guide means (2) comprise two lateral elements arranged at the two sides of the stem (1) and inserted in the body for receiving (3) through two holes (32) arranged the sides of the first threaded hole (31), said lateral elements (2) being both provided with said appendix (20).

The guide means (2) contribute to the correct positioning and to the correct handling of the orthodontic screw (100) not only because their respective lateral elements are inserted in the holes (32) of the body (3), but also for the appendixes (20) that are arranged at the sides of the driving portion (11).

As shown in FIGS. 4 and 5, a positioning element or tab (6) is provided, formed by two parts or semi-tabs (60, 61) that can be used to support the orthodontic screw (100) during the formation of the orthodontic plate and to protect the activation holes (12) that, in this way, will not be filled by the resin; the tab (6) is provided with at least one appendix (62) stably insertable in a cavity (12) of said screw (100). In particular, the appendix (62) is constituted by a cylindrical body (in this example, one for each portion of the tab 6) insertable into one of the holes (12) of the driving portion (11); in this way, during the formation of plate the elements destined to form the orthodontic appliance are firmly kept united to each other, and the resin is prevented from penetrating into the holes (12).

The two parts (60, 61) of the tab (6) are provided with means allowing their stable but reversible coupling. According to the example shown in the drawings, the upper part (60) is provided, in its lower part, with two recesses (66) symmetrically arranged above two corresponding teeth (65). Correspondingly, the lower portion (61), in its upper part, is provided with two flexible appendices (63) which are superiorly shaped complementarily with respect to the recesses (66), and that form two inner recesses (64) shaped complementarily with respect to the teeth (65) of the upper portion (60). Between the two teeth (65) and the two appendixes (63) there are arranged the appendixes (62) which are intended to be introduced into the holes (12) of the driving portion (11). In this way, once introduced the appendix (62) of one of the two portions (60, 61) in one of the holes (12), it is possible to "close" the tab (6) approaching the other portion (61, 60) so as to join the same portions by distancing the resilient appendages (63) and inserting them into the recesses (66). This allows a convenient handling of the orthodontic screw (100) retained and supported by the tab (6) and an easy release of the same.

Figure 8:
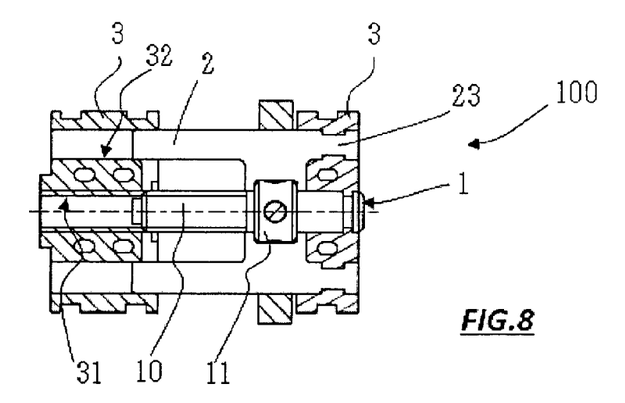
FIGS. 8 and 9 are plan views showing other embodiments of a screw according to the present invention, respectively, in the form of a mono-directional expansion screw (FIG. 8) and three-directional expansion screw (FIG. 9); the drawings show plan views with sectioned and with the screws in a configuration of maximum expansion.
Figure 9:
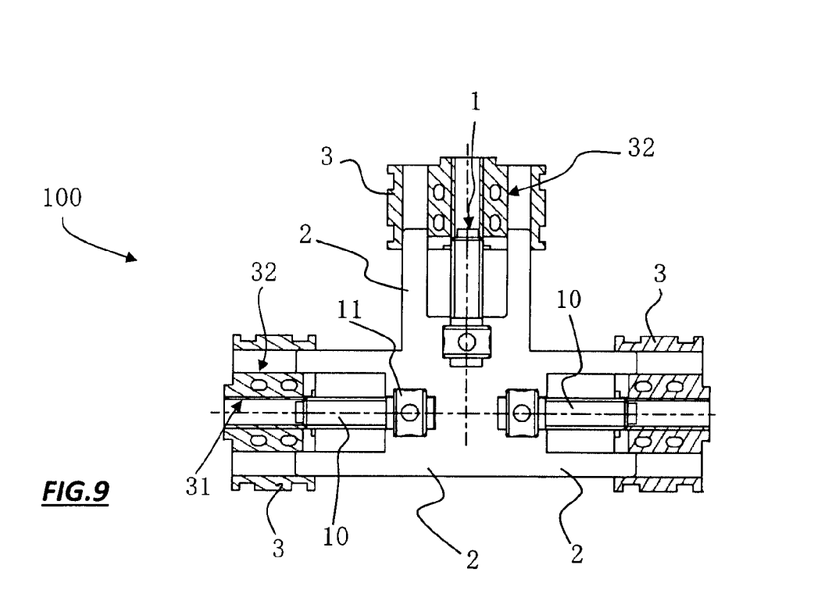

As represented by way of example in FIGS. 8 and 9, the present invention can also be applied to the mono-directional and three-directional screws, not only to bidirectional screws such as that described previously, as well as in other screws not shown such as, for example, the so-called "fan-like" orthodontic screws. In particular, the example shown in FIG. 8 relates to an unidirectional orthodontic screw, marked with (100), wherein the guide element (2) has a connecting portion (23) on the side opposite to that from which emerges the threaded stem portion (10); in practice, the portion (23) of the guide element (2) is integral with the corresponding body portion (3) disposed on the right in the drawing, while the part of the guide element (2) arranged to the left in the drawing is allowed to slide relative to the body (3) inside the hole (32), as provided for the bidirectional screw previously described. In the case of unidirectional orthodontic screw, the threaded stem portion (10) will be engaged only on one side (the left side in the drawing) with the corresponding hole (31). The screw (100) represented in FIG. 9 is of the three-directional type, with three stems (1) operable in an independent manner, each of which has a respective threaded stem portion (10) passing through a corresponding receiving body (3) and a driving portion (2). Similarly, the principle of the present invention can be applied to so-called "fan-like" orthodontic screws having two hinged arms that can be connected to the threaded stem portion of a screw also provided with a driving portion. An orthodontic screw of this type is disclosed in IT-0001278739 to which reference can be made for further details.

Figure 10:
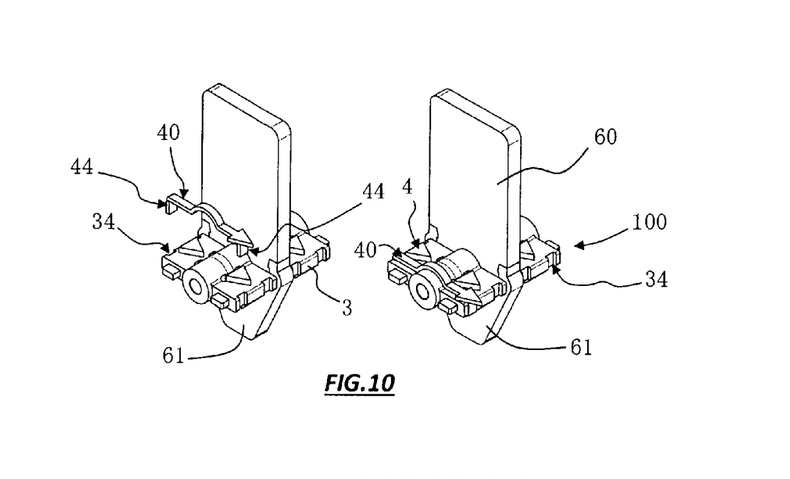
FIG. 10 is a perspective view of another example of orthodontic screw according to the present invention, shown in the assembled configuration together with the tool for its handling, and in which indicators of the direction of activation of the screw are provided.

The screws (100) are provided with the indicator elements (4) that can be used, as usual, to provide the activation direction of the screw, or to indicate the direction of rotation to be used to "open" the screw, that is to lengthen it. In the example shown in FIG. 10, the indicator elements (4) is associated with an additional indicator (40) which has the shape of an arrow and is provided with two teeth (44) that can be inserted in corresponding seats (34) presented by the body (3). The additional indicator (40), which can be realized in a different color, is much more visible than the conventional indicator (4); in particular, when the plate is in the oral cavity, the additional indicator shows in a very evident way the correct direction for the activation of the screw.

Figure 14:
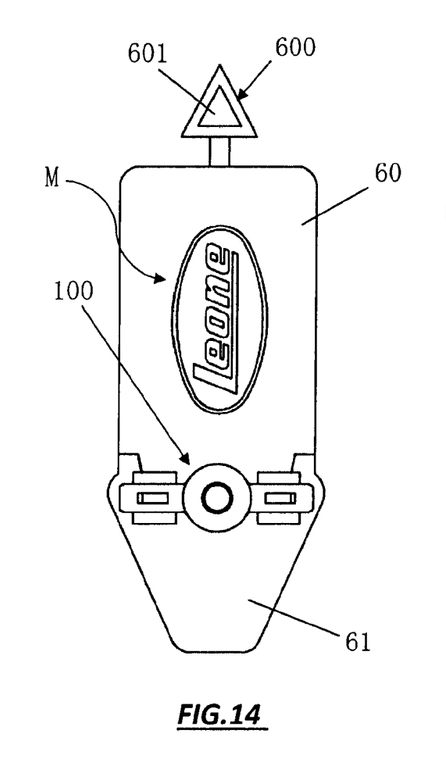
FIGS. 14 and 15 show another embodiment of an orthodontic appliance manufactured in accordance with the present invention.
Figure 15:
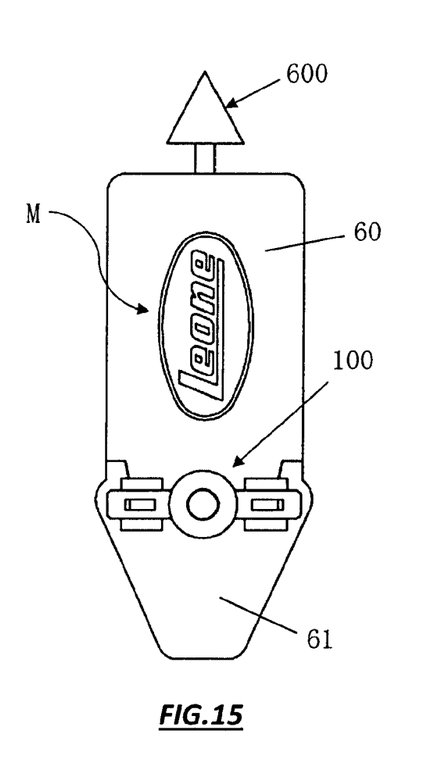

According to the example shown in FIGS. 14 and 15, the upper semi-tab (60) has an appendix (600) on its upper side (the side opposite to that of association with the screw). Said appendix (600) is of triangular shape and, on its rear side, has a depression (601) that is also triangular in shape and has dimensions corresponding to those of the indicators (4) previously mentioned. The appendix (600) can be easily detached and fitted on an indicator (4) before being embedded in the technopolymer. The depression (601) on the back of the appendix (600) facilitates this operation. In this way, it is provided a further and most noticeable indication of the direction of activation of the expansion screw, in particular when the tab (6), and thus the appendix (600), is made of a material having a color contrasting with that of the technopolymer of said receiving body.

It is understood that, more in general, the depression (601) has the shape and dimensions corresponding to those of the indicators (4) which may also be non-triangular although it is believed that the triangular shape is particularly suitable to indicate the direction of activation of the screw.

The materials used to make the present orthodontic appliance are biocompatible. On the sides of the tab (6) can be imprinted the name of the manufacturer or any other sign (M).

The invention is not limited to the examples described and illustrated above, but it may vary as regards the nature and arrangement of its parts, without departing from the inventive teaching here disclosed and claimed.

The invention claimed is:

1. An expansion screw for orthodontic appliances, the expansion screw comprising:
   at least one stem with at least a threaded portion extending along a longitudinal extension of said at least one stem;
   at least one receiving body for receiving said threaded portion provided with a receiving hole complementarily shaped with respect to said threaded portion so as to allow screwing of said threaded portion;
   a guide means for guiding said at least one receiving body;
   a driving means for driving said stem, said driving means comprising a cylindrical driving portion formed on said stem and provided with driving holes for obtaining rotation of said stem for operation of the orthodontic screw by a tool configured to be inserted into said driving holes;
   a positioning tab composed of multiple parts associated with each other to support said expansion screw when an orthodontic appliance is made, said positioning tab being provided with at least one appendix configured to be interlocked to said expansion screw with said at least one appendix being inserted into one of said driving holes.

2. The expansion screw according to claim 1, wherein said multiple parts comprises two multiple parts.

3. The expansion screw according to claim 2, wherein said two multiple parts are on diametrically opposite sides with respect to said at least one stem.

4. The expansion screw according to claim 3, wherein said two multiple parts have an upper part and a lower part, and said upper part is provided, on a lower side thereof, with two upper recesses arranged above corresponding symmetrical teeth, and correspondingly, said lower portion, on an upper side thereof, is provided with two flexible appendices that are shaped complementarily with respect to said two upper recesses, and inside said two flexible appendices are two recesses complementarily shaped with respect to said symmetrical teeth of said upper part.

5. The expansion screw according to claim 4, wherein said at least one appendix comprises a first appendix and a second appendix, wherein said first appendix is arranged between said symmetrical teeth and said second appendix is arranged between said two flexible appendices, said first appendix and said second appendix being adapted to be introduced into any one of said driving holes.

6. The expansion screw according to claim 1, further comprising:
   at least one pointer or indicator adapted to indicate a direction of activation.

7. The expansion screw according to claim 6, wherein said at least one pointer or indicator is removably associated with said positioning tab.

8. The expansion screw according to claim 6, wherein said at least one pointer or indicator is removably associated with an upper part of said positioning tab.

9. The expansion screw according to claim 1, wherein said receiving hole of said at least one receiving body has a longitudinal extension substantially corresponding to that of said threaded portion of said at least one stem.

10. The expansion screw according to claim 9, wherein said guide means comprises two lateral elements disposed on opposite sides of said at least one stem and inserted into two holes, in the receiving body, arranged on opposite sides of said receiving hole, said lateral elements being provided with an appendix.

11. The expansion screw according to claim 1, wherein said guide means comprises a flat body, said flat body having a cross section with a first dimension less than a second dimension.

12. The expansion screw according to claim 1, wherein said driving portion extends along said stem for a first distance and protrudes, with respect to said stem, for a second distance, and said guide means comprises an appendix, adapted to interact with said driving portion, provided with a cavity having a rectangular profile and extends along a longitudinal direction of said at least one stem and radially with respect the longitudinal direction, said rectangular profile having dimensions corresponding respectively to said first distance and said second distance.

13. An expansion screw for orthodontic appliances, the expansion screw comprising:
a stem comprising a stem longitudinal extension, said stem comprising at least a threaded portion extending along said longitudinal extension;
a receiving body for receiving said threaded portion, said receiving body comprising a receiving hole, said receiving hole having a receiving hole shape corresponding to a shape of said threaded portion, wherein said threaded portion is rotatable in said receiving hole;
a guide means for guiding said at least one receiving body;
a driving means for driving said stem, said driving means comprising a cylindrical driving portion formed on said stem, said cylindrical driving portion comprising cylindrical driving portion holes for receiving a tool to rotate the cylindrical driving portion;
a positioning tab comprising a plurality of position tab parts to support said expansion screw when an orthodontic appliance is formed, at least one of said plurality of position tab parts comprising a projection, one of said cylindrical driving holes receiving said projection when the orthodontic appliance is formed.

14. The expansion screw according to claim 13, wherein said plurality of position tab parts are on diametrically opposite sides with respect to said stem.

15. The expansion screw according to claim 14, wherein another one of said plurality of position tab parts comprises another projection, said another projection being located opposite said projection.

16. The expansion screw according to claim 15, wherein said one of said plurality of position tab parts is one of an upper part and a lower part and said another one of said plurality of position tab parts is the other one of said upper part and said lower part, and said upper part is provided, on a lower side thereof, with two upper recesses arranged above corresponding symmetrical teeth, and correspondingly, said lower portion, on an upper side thereof, is provided with two flexible appendices that are shaped complementarily with respect to said two upper recesses, and inside said two flexible appendices are two recesses complementarily shaped with respect to said symmetrical teeth of said upper part.

17. The expansion screw according to claim 16, wherein said projection and said another projection are arranged between said symmetrical teeth and said two appendices.

* * * * *